United States Patent [19]

Eyal et al.

[11] Patent Number: 6,160,173
[45] Date of Patent: Dec. 12, 2000

[54] PROCESS FOR THE RECOVERY OF LACTIC ACID ESTERS AND AMIDES FROM AQUEOUS SOLUTIONS OF LACTIC ACID AND/OR SALTS THEREOF

[75] Inventors: Aharon Meir Eyal, Jerusalem, Israel; Patrick R. Gruber, Blaine, Minn.; Paul McWilliams, Racine, Wis.; David R. Witzke, Cambridge, Mass.

[73] Assignee: Cargill Incorporated, Wayzata, Minn.

[21] Appl. No.: 09/284,108

[22] PCT Filed: Oct. 2, 1997

[86] PCT No.: PCT/US97/17775

§ 371 Date: Oct. 26, 1999

§ 102(e) Date: Oct. 26, 1999

[87] PCT Pub. No.: WO98/15519

PCT Pub. Date: Apr. 16, 1998

[30] Foreign Application Priority Data

Oct. 9, 1996 [IL] Israel ........................................ 119388

[51] Int. Cl.⁷ ........................ C07C 51/487; C07C 51/493
[52] U.S. Cl. ........................ 562/589; 562/580; 560/179; 564/201; 549/273
[58] Field of Search ........................ 562/580, 589; 560/179; 564/201; 549/273

[56] References Cited

U.S. PATENT DOCUMENTS

| 4,275,234 | 6/1981 | Baniel et al. ........................ 562/584 |
| 4,282,323 | 8/1981 | Yates ........................ 435/140 |
| 4,405,717 | 9/1983 | Urbas ........................ 435/140 |
| 4,444,881 | 4/1984 | Urbas ........................ 435/139 |
| 5,071,754 | 12/1991 | Walkup et al. . |
| 5,132,456 | 7/1992 | King et al. . |
| 5,252,473 | 10/1993 | Walkup et al. . |
| 5,510,526 | 4/1996 | Baniel et al. . |

FOREIGN PATENT DOCUMENTS

| 0159285 | 3/1985 | European Pat. Off. . |
| 0159585 | 10/1985 | European Pat. Off. . |
| 0517571 | 12/1992 | European Pat. Off. . |
| 46-30176 | 9/1971 | Japan . |
| 9300440 | 1/1993 | WIPO . |
| 9730964 | 8/1997 | WIPO . |

OTHER PUBLICATIONS

Derwent's Abstract of JP 7–258,154 of Oct. 1995.

*Primary Examiner*—Howard C. Lee
*Assistant Examiner*—Leigh C. Maier
*Attorney, Agent, or Firm*—Ladas & Parry

[57] ABSTRACT

The invention provides a process for the recovery of purified lactic acid values from an aqueous feed solution containing lactic acid, lactic acid salt, or mixtures thereof, comprising: bringing the feed solution into contact with a substantially immiscible anion exchanger to form a substantially water-immiscible phase comprising an anion exchanger-lactic acid adduct; effecting a condensation reaction in the substantially water-immiscible phase between a carboxylic moiety of the lactic acid adduct and a moiety selected from a hydroxyl moiety and a primary or secondary amine moiety to respectively form a lactic acid ester or amine product; and separating the formed lactic acid product from the anion exchanger.

39 Claims, No Drawings

PROCESS FOR THE RECOVERY OF LACTIC ACID ESTERS AND AMIDES FROM AQUEOUS SOLUTIONS OF LACTIC ACID AND/OR SALTS THEREOF

This application is a 371 of PCT/US97/17775 filed on Oct. 2, 1997.

The present invention relates to a process for the recovery of lactic acid. More particularly, the present invention relates to a process for the recovery of lactic acid from an aqueous solution containing lactic acid, lactate salts, or mixtures thereof.

Lactic acid has long been used as a food additive and in various chemical and pharmaceutical applications. More recently, lactic acid has been used in the making of biodegradable polylactic acid polymers as a replacement for present plastic materials, as well as for various new uses where biodegradability is needed or desired. Accordingly, there is an ever-increasing demand for lactic acid. The present invention aims at meeting this demand by providing an efficient and environmentally friendly process for producing lactic acid which avoids the consumption of bases and acids and substantially reduces, if not eliminates, the formation of waste or byproduct salts.

The production of lactic acid is commonly carried out by fermentation of a strain of the bacterial genus Lactobacilus, and more particularly, for example, by the species *Lactobacillus delbrueckii* or *Lactobacillus acidophilus*. In general, the production of lactic acid by fermentation in a fermentation broth is well known in the art. The fermentation substrate consists of carbohydrates together with suitable mineral and proteinaceous nutrients. Because the lactic acid-producing microorganisms are inhibited in a strongly acidic environment, the pH of the fermentation broth is usually kept above 4.5, preferably within the range of about 5.0 to 7.0, more preferably within the range of about 5.5 to 6.5, and most preferably within the range of about 6.0 to 6.5., although fermentation in a pH range of about 3.8–4.5 has also been carried out. To maintain this pH level, suitable water-soluble basic substances or agents that are non-toxic to the acid-producing microorganism, such as alkali metal hydroxides, carbonates, or bicarbonates, or alkaline earth metal hydroxides or carbonates, are commonly added to the fermentation broth to neutralize the acid being produced. This results in the formation of a lactate solution rather than the desired lactic acid product. Such a lactate solution contains the lactate anion and the corresponding cation of the substance used to neutralize the fermentation broth.

Various methods have been proposed for the recovery of lactic acid from a fermentation broth. When the fermentation is carried out in the presence of calcium carbonate, it is possible to recover the lactic acid by acidification with sulfuric acid. This results in the precipitation of calcium sulfate, while free lactic acid remains in the mother liquor. If desired, the mother liquor may be concentrated to up to about 90 wt % lactic acid. Subsequently, lactic acid may be extracted from the mother liquor with a suitable organic extractant, to yield an extract which is back-extracted with water, or the acid may be adsorbed on a suitable adsorbent and later desorbed. The resulting aqueous lactic acid solution may then be concentrated. This method has the disadvantage that it irreversibly consumes calcium carbonate and sulfuric acid and leaves, as waste, large quantities of calcium sulfate which give rise to disposal problems.

U.S. Pat. No. 5,132,456 (King, et al.), describes a process for recovering carboxylic acid from a carboxylic acid-containing aqueous feed stream having a pH close to or above the $pK_a$ level of the acid. The recovery of that process involves what may be described as a cascade-type acid withdrawal operation, in which the basicity of the extractant is increased stepwise. In a first stage of the process, the feed stream is contacted with an adsorbent such as a strongly basic extractant or a solid anion exchanger. In a second stage, the acid-loaded adsorbent is contacted with an aqueous solution of ammonia or a low molecular weight trialkyl amine having a stronger affinity to the carboxylic acid that is being recovered than that of the adsorber used in the first stage. In this way, an aqueous solution of a water-soluble carboxylic acid ammonium salt is formed. This is then subjected to heat treatment, whereby the salt is decomposed to yield back the trialkyl amine or ammonia and free carboxylic acid. Applying this process to lactic acid involves the formation of salts of lactic acid with strong bases having a $pK_a$ value of about 9–11. Thus, the decomposition of these salts into free lactic acid is energy intensive. Examples 12–14 of said U.S. patent mention the use of Alamine 336 (tricaprylylamine) for the extraction of, among others, lactic acid from an aqueous solution, but no yields are mentioned. By the extraction of even small quantities of lactic acid from a fermentation broth, the pH of the broth rises rapidly to above 7 while the pKa of an extractant based on Alamine 336 is less than 6. As shown in FIGS. 3 and 4 of said patent, the uptake of carboxylic acids from aqueous solutions drops rapidly with an increase of the pH. It is therefore inherent in these examples that the lactic acid uptake, if any, is negligible. It is further noted that upon heat treatment and concentration of an ammonium lactate, crystalline lactic acid does not precipitate; instead, the viscosity of the solutions increases steadily as a result of self-association of the acid. It is thus evident that the process of U.S. Pat. No. 5,132,456 is unsuitable for the recovery of lactic acid from a fermentation broth.

U.S. Pat. Nos. 4,444,881 and 4,405,717 (Urbas) describe a process for the recovery of an organic acid from a diluted aqueous solution of its calcium salt by adding a water-soluble trialkyl amine carbonate to the solution, to form, on the one hand, a water soluble trialkyl ammonium salt of the acid, which salt remains in solution; and, on the other hand, calcium carbonate which precipitates. After removal of the calcium carbonate, the remaining mother liquor is heated for the separate recovery of the amine and the product acid. The water-soluble trialkyl amines employed in accordance with these patents are strongly basic. Accordingly, the decomposition of the trialkylammonium salts into free acids is energy-intensive.

U.S. Pat. No. 4,282,323 (Yates) describes a process for obtaining lower carboxylic acids from a salt solution of carboxylic acid obtained from fermentation. The process appears to be applicable to a restricted number of lower aliphatic and aromatic monocarboxylic acids and is specifically described only in relation to acetic acid. In accordance with that process, the aqueous solution of a carboxylic acid salt is contacted with pressurized carbon dioxide in the presence of a liquid polar organic solvent having a boiling point of from −30C to 90C serving as extractant, to convert at least part of the salt to the corresponding free acid, which is then taken up by the organic phase, from where it is subsequently recovered. It is inherent in the use of a polar organic extractant that the bulk of the carboxylic acid remains in the neutral to basic aqueous phase, and indeed the recovery rates reported in U.S. Pat. No. 4,282,323 are low, ranging between 4.8–18% of the acid initially present.

U.S. Pat. No. 4,275,234 (Baniel, et al.) is directed to a method of recovering various acids in their free form from aqueous solutions. Thus, the process of Baniel is not applicable to a lactate solution of the type commonly obtained from a fermentation process conducted at a pH higher than the pKa of the acid or from other sources. The essence of the Baniel patent is the discovery that efficient back-extraction can be achieved by performing the back-extraction at a temperature higher than that of the primary extraction.

R. Bar and J. I. Geiner, *Biotechnology Progress,* Vol. 3, p. 109 (1987) studied the feasibility of extracting lactic acid from aqueous solution by means of a long-chain trialkyl amine of low basicity, such as tridodecylamine, using various tridodecylamine solutions in n-dodecanol. It was found that extraction of lactic acid with a long-chain trialkyl amine such as tridodecylamine was effective only at a pH that is lower than the $pK_a$ of lactic acid, the latter of which is 3.86. At such a low pH, however, the lactic acid fermenting microorganism such as, for example, *Lactobacillus delbrueckii* or *Lactobacillus acidophilus* is severely inhibited.

Free lactic acid can also be purified by forming its esters through condensation, purifying those esters by distillation or by extraction, and then hydrolyzing them back to lactic acid. Such condensation is usually catalyzed by an acidic medium.

As indicated above, lactic acid fermentation is conducted at about neutral pH. Since the pKa of lactic acid is 3.86, at the pH of fermentation, mostly lactate salts exist. Substantially complete recovery and purification of lactic acid from the fermentation liquor through esterification may require acidulation by a strong acid that displaces lactic acid from its salt and frees it to react with an alkanol to form the ester. Nakanishi and Tsuda (JP 46/30176) consider production of 1-butyl lactate by extraction of an acidified crude fermentation broth with 1-butanol, followed by esterification of the extract phase. BASF (EP 159285) considers a similar process with isobutanol to form isobutyl lactate.

In WO 93/00440, assigned to DuPont Corporation, there is described a process which comprises the steps of: (1) simultaneously mixing a strong acid, an alcohol, and a concentrated fermentation broth which contains mainly basic salts of lactic acid, which react to form a crystal precipitate comprising basic salts of the strong acid and an impure lactate ester of the alcohol; (2) removing water from the mixture as a water/alcohol azeotrop, which can be accomplished either sequentially or substantially simultaneously with step (1); removing the crystal precipitate from the mixture; (4) distilling the impure lactate ester to remove impurities; and (5) recovering the high purity ester.

Acidulation of the fermentation broth prior to esterification results in consumption of reagents and in production of undesired by-product salts.

Liquid-liquid extraction (LLE) proved to be an efficient way to recover carboxylic acids from contaminated aqueous solutions. It is particularly suitable for recovery of acidic fermentation products from fermentation liquors. Thus, a large fraction of the world's citric acid production uses an LLE process to recover the acid from the broth by extraction with an extraction composed of a water immiscible amine in a diluent. This extractant combines high recovery yields, high selectivity and reversibility, resulting in high yields of recovery of pure product at relatively high concentration. As stated hereinbefore, Baniel, et al. (U.S. Pat. No. 4,275,234) have found that the extracted acid can be recovered from the acid comprising extractant (extract) by back-extraction with water. They have also found that, if the back-extraction is conducted at a temperature higher than that of the extraction, the concentration of the acid in the backextract (the aqueous product of the back-extraction) could be significantly higher than that of the aqueous feed to the process.

Yet, if the concentration of the acid in the feed is very low, the concentration of the back-extract could still be too low. That is particularly true when the feed consists mainly of the salt of the acid rather than the free acid.

Acidulating neutral fermentation liquors by the addition of acids for recovery via ester formation or other methods, results in the formation of by-product salts, such as gypsum in the case of calcium lactate acidulation with sulfuric acid or sodium, or ammonium sulfate in others. Reagents are consumed and disposal of undesired by-products is required. Efforts have recently been made to recover lactic acid from fermentation liquors without formation of by-product salts. Such processes will be referred to hereinbelow as salt splitting processes. In some recently published patents, LLE is applied for salt splitting. Thus, as mentioned above, in U.S. Pat. No. 5,132,456, a strongly basic extractant extracts part of the lactic acid from the neutral solution, which results in a lactic acid loaded extractant and a basic solution. This basic solution, which still comprises most of the lactic acid values, could be recycled as a neutralizing medium to the fermentation. In U.S. Pat. No. 5,510,526 (Baniel, et al.), the extraction of the acid is conducted under $CO_2$ pressure so that a bicarbonate is formed. The latter can be used as a neutralizing agent in the fermentation. In order to limit the $CO_2$ pressure to an economic one and still achieve high yields, the extractant used should be quite strong.

In fact, any LLE based salt splitting process that avoids the production of (neutral) by-product salts would require a strongly basic extractant. These extractants are usually composed of an amine as the main active component. The preferred amines are chosen from the group of primary, secondary or tertiary amines, with a total number of at least 18 carbon atoms. Mostly preferred are tertiary amines. A diluent is usually used to achieve the required physical properties. The basicity of the extractant is easily adjusted by adding a polar solvent to the extractant. Such polar solvents enhance the extraction efficiency of the amine, and are usually referred to as enhancers. Alkanols provide very efficient enhancers. The basicity of the extractant is thus adjusted by the amount of the enhancer in the extractant or, more precisely, by the enhancer-to-amine molar ratio. In the strongly basic extractants used in salt splitting processes, the enhancer-to-amine molar ratio is usually at least 1:1, and in many cases is higher than that.

Such strong extractant holds strongly to the extracted lactic acid. Recovery of the extracted acid by washing with an aqueous solution of a base is feasible, but forms the lactate salt of the base. It is therefore not practical in those cases where lactic acid or its esters are the desired product. Back-extraction with water forms a dilute product (back-extract).

As mentioned above, U.S. Pat. No. 5,132,456 suggests a way to recover extracted carboxylic acid from a strong extractant, comprising leaching or back-extraction with an aqueous solution of ammonia or low molecular weight alkyl amine, especially trimethyl amine (TMA). The resultant aqueous ammonium or alkyl ammonium carboxylate solution can be concentrated, if necessary, and the carboxylate can be decomposed thermally to yield the product carboxylic acid and ammonia or amine which can be condensed and recycled. This process is costly and complex, and it is particularly problematic for recovery of extracted lactic acid:

"For lactic acid the decomposition is incomplete, being stopped by the formation of a viscous, almost glassy mass containing polymerized lactic acid along with substantial TMA and water. There are, however, effective ways of driving the decomposition to completion for lactic acid, such as diluting the viscous mass with an appropriate solvent (e.g. methyl isobutyl ketone) and continuing the heating and decomposition process."

With this state of the art in mind, there is now provided, according to the present invention, a process for the recovery of purified lactic acid values from an aqueous feed solution containing lactic acid, lactic acid salt, or mixtures thereof, comprising: a) bringing said feed solution into contact with a substantially immiscible anion exchanger to form a substantially water-immiscible phase comprising an anion exchanger-lactic acid adduct; b) effecting a condensation reaction in said substantially water-immiscible phase between a carboxylic moiety of said lactic acid adduct and a moiety selected from a hydroxyl moiety and a primary or secondary amine moiety to respectively form a lactic acid ester or amine product; and c) separating the formed lactic acid product from the anion exchanger.

In a first preferred aspect of the present invention, there is provided a process for the recovery of purified lactic acid values from an aqueous feed solution containing lactic acid, lactic acid salt, or mixtures thereof, comprising bringing said feed solution into contact with a substantially immiscible anion exchanger to form a substantially water-immiscible phase comprising an anion exchanger-lactic acid adduct, effecting a condensation reaction in said substantially water-immiscible phase between a carboxylic moiety of said lactic acid adduct and a hydroxyl moiety to form a lactic acid ester and separating the formed lactic acid ester from the anion exchanger.

In a second preferred aspect of the present invention there is provided a process for the recovery of purified lactic acid values from an aqueous feed solution containing lactic acid, lactic acid salt, or mixtures thereof, comprising: a) bringing said feed solution into contact with a substantially immiscible anion exchanger to form a substantially water-immiscible phase comprising an anion exchanger-lactic acid adduct; b) effecting a condensation reaction in said substantially water-immiscible phase between a carboxylic moiety of said lactic acid adduct and a reagent comprising a primary or secondary amine moiety to form an amide of lactic acid; and c) separating the formed amide of lactic acid from the anion exchanger.

In a first preferred embodiment of the present invention said anion exchanger is a basic extractant comprising a water immiscible amine as the main active component, and there is formed a substantially water-immiscible extract phase comprising an anion exchanger-lactic acid adduct.

In a second preferred embodiment of the present invention said anion exchanger is a solid anion exchanger.

In preferred embodiments of the present invention said aqueous feed solution results from fermentation and is at a pH of at least 4.5.

The process of the present invention is based upon the surprising finding that lactic acid held in a strong extractant can be condensed, thereby losing the acid function, and in preferred embodiments of the present invention the separated lactic acid ester has a purity of at least 99%.

The term "lactic acid values" as used herein is intended to denote lactic acid and its products, mainly condensation products such as esters with alkanols, lactides, oligomers or polymers of lactic acid and amides of lactic acid.

In preferred embodiments of the present invention said lactic acid salt is selected from a group consisting of sodium, calcium, ammonium lactate and mixtures thereof.

In the organic phase formed on extraction, the lactic acid is bound to a basic amine. In fact, it is believed that the organic phase formed on the extraction by an amine comprises, instead of lactic acid, a salt-amine lactate. That is particularly true in the case of an extractant of at least a moderate strength with an apparent basicity corresponding to a pKa of at least 3.5, and in the case where the lactic acid content in the extract is such that the lactic acid-to-amine ratio is lower than one. By analogy, to the above-mentioned DuPont patent, one would expect that a strong acid addition would be required to effect the esterification. The addition of such strong acid would liberate the extracted lactic acid and would allow esterification, but at the cost of forming the amine salt of the strong acid in the organic phase. Regeneration of the amine from that salt would have been required to allow reuse as an extractant. Such regeneration would require contact with a base solution and would form a by-product salt of the strong acid.

Thus, compared to the DuPont process, the process in the present invention has several advantages, including avoidance of by-product salt formation and saving on energy used for water evaporation.

In the condensation reaction, a carboxylic moiety reacts with an hydroxyl moiety to form an ester or with a reagent comprising a primary or secondary amine moiety to form an amide. In both cases a water molecule is formed as a by-product. Thus, the presence of water drives the equilibrium towards the opposite direction, i.e. hydrolysis. In the DuPont process, the fermentation liquor needs to be concentrated prior to the reaction. In the examples used in that patent, the broth is concentrated up to about a water content of 25–28%. This corresponds to distillation of about 6 to 9 tons of water per ton of lactic acid in the product.

In the present process, the condensation is effected in an organic phase which is formed upon bringing the feed solution into contact with an amine based basic extractant. The solubility of water in the extractant is small. Some water co-extracts with the lactic acid, but that is limited to about one mole of water per mole of lactic acid (compared to about 2.5 in the concentrated solution used in the example of the DuPont patent). Thus, the extraction provides for the removal of water in addition to the separation of lactic acid from the impurities, which is equivalent to that obtained by distilling about 7 to 9 tons of water per ton of lactic acid in the product. In addition, water formed in the esterification is removed in the DuPont patent by distilling an azeotrop, while in the present invention the water formed is rejected from the organic phase as it does not dissolve there. Yet, if desired for accelerating the esterification, the system of the present invention lends itself to easy water removal. Co-extracted water can be removed prior to effecting the condensation to leave a practically anhydrous medium. Water formed in the condensation could be removed either sequentially, or substantially simultaneously with the condensation reaction by distillation, as water or as an azeotrop, with possible use of a carrier gas or at sub-atmospheric pressure.

The basicity of water soluble bases is easily determined by their degree of dissociation in an aqueous solution. The basicity of water immiscible extractants is determined indirectly, through their interaction with solutes in an aqueous solution. Thus, the apparent basicity of highly basic extractants can be compared by contacting them with aqueous solutions of NaCl and determining the pH of the aqueous solution in equilibrium. The higher the pH, the stronger the apparent basicity of the extractant. For comparing extractants of medium or weak basicity, equilibration with acid solutions is preferred. Unlike water soluble bases, the apparent basicity found for water immiscible extractants is determined, in addition to the properties of the amine, by the acid in the aqueous solution, by steric hindrance to extraction, and by the diluents of the amine.

In preferred embodiments of the present invention said contact with a substantially immiscible basic extractant forms, in addition to the amine lactic acid adduct, a basic product, which basic product is preferably selected from the group consisting of ammonia, carbonates and bicarbonates of ammonioa, of alkali and of alkaline earth metals.

Also preferred are embodiments wherein said contact with a substantially immiscible basic extractant is conducted in a $CO_2$ atmosphere.

The condensation reaction is accelerated at elevated temperatures. Thus, it is preferably conducted at a temperature of at least 100° C. and more preferably at a temperature of at least 140° C.

Said condensation is preferably also conducted in the presence of a catalyst, e.g. tin ions, toluene sulfonic acid, sulfuric acid, titanium, Lewis acid catalysts and non-oxidizing strong acid catalysts.

Similarly, said condensation reaction can be conducted at sub-atmospheric pressure and/or in the presence of a carrier gas.

In the ester forming condensation reaction, the carboxylic moiety of the lactic acid reacts with an hydroxyl moiety. Lactic acid is an hydroxycarboxylic acid. Therefore, the hydroxyl moiety could be on a second lactic acid molecule forming one of the lactic acid condensation products, which could be a dimer, e.g. lactide, trimer or oligomer. The hydroxyl moiety could also be of another molecule, e.g., an alkanol, and in preferred embodiments of the present invention said alkanol is present in the basic extractant used for lactic acid extraction, where it can act as an extraction enhancer, and thereafter said alkanol is present in the extract. In these cases, the alkanol has a double role, as an enhancer and a reagent for esterification. Otherwise, or in addition, an alkanol can be added to the extract prior to effecting the condensation reaction. The added alkanol can be the alkanol used as the enhancer or a different one. Reaction of the extracted lactic acid with an alkanol that also provides an enhancer has an additional benefit: it consumes the alkanol, decreases its proportion in the extract, and thereby releases more lactic acid for further esterification.

In the amide-forming condensation reaction the carboxylic moiety of the lactic acid reacts with a reagent comprising a primary or secondary amine moiety to form an amide. The reagent is preferably of a low molecular weight. Such amide should be a product of a reaction with a reagent molecule and not with cation exchanger, which in many cases carry amine functional groups. Therefore these functional groups of the cation exchangers are preferably tertiary or quaternary amines.

U.S. Pat. No. 5,132,456 uses ammonia or alkyl amine to recover carboxylic acid bound to a sorbing phase. Yet, there the recovery is effected by forming the salt of the carboxylic acid rather than the amide as described in claim 1: "(c) contacting the separated acid-sorbing phase with an aqueous solution of low molecular weight alkyl amine or ammonia, thereby solubilizing said carboxylic acid from the sorbing phase into said aqueous solution as alkylammonium or ammonium carboxylate, . . . ". The difficulties involved with the formation of these salts were described earlier (see page 9).

On condensation, the lactic acid loses its carboxylic function and thereby detaches from the anion exchanger. The ester or amid formed can be considered a neutral molecule, or at least as having an acidity much lower than the lactic acid. Therefore, it does not interact strongly with the anion exchanger and its separation from the basic extractant is easy. Thus, esterification obviates the need of the very complex and costly recovery process suggested in U.S. Pat. No. 5,132,456.

Water formed in said condensation reaction can be removed either sequentially or substantially simultaneously with said condensation reaction and the lactic acid ester or amide formed in the condensation reaction can be separated from the anion exchanger after effecting the reaction or during the condensation. Separation during the condensation accelerates the reaction. The ester or amide could be separated by transfer into a solvent which is immiscible with the anion exchanger or has low miscibility with it. Alternatively, if the lactate ester or amide has significant solubility in water, it can be washed out of the extract after the condensation to form an aqueous solution of the ester or amide. Another option is distilling the lactic acid ester or amide into the vapor phase, either during the reaction or after it. Such separation into the vapor phase could be assisted by operation at subatmospheric pressure or by transfer of a carrier gas. In that case, if an amine containing extractant is used as the anion exchanger, the amine's volatility is preferably lower than that of the ester or amide. Condensation products of suitable molecular weight and polarity may not be soluble in the lactic acid depleted organic phase and may precipitate out of it.

The lactic acid ester could be used as is, e.g. as a "green" solvent; converted to other esters, e.g. through trans-esterification; reacted to form polylactic acid or other polymers or hydrolyzed to recover lactic acid. Thus, said lactic acid ester can be used to form lactoyl lactate or lactide. In preferred embodiments of the present invention said lactide contains less than 20 milliequivalents of free acid and is suitable for direct use in the production of polylactic acid without the need for further purification. In those cases where the ester was formed from lactic acid and an alkanol it is hydrolyzed to lactic acid and the alkanol. Hydrolysis is simply conducted by contact with water or with an aqueous solution. In those cases where the ester is separated into an aqueous solution, hydrolysis could be effected in the ester solution formed and induced by the water presence. The alkanol formed on hydrolysis, as well as on other treatments of the ester such as trans-esterification or condensation, can be separated and reused in a condensation reaction, e.g. by reintroduction into the extractant prior to the extraction of more lactic acid or into the extract.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

An extractant composed of 47 wt % tricaprylyl amine (Henkel's Alamine 336), 33 wt % octanol and 20 w % kerosene was contacted with an aqueous solution of lactic acid. An extract containing 11 wt % lactic acid was formed. This extract was heated in a closed pressure vessel to 160° C. and kept at this temperature for 4 hours. At the end of the heating, the organic phase contained 15.4 wt % octyl lactate, i.e. more than 60% of the extracted lactic acid reacted with the octanol present in the organic phase to form the ester.

EXAMPLE 2

An extractant composed of 47 wt % tricaprylyl amine (Henkel's Alamine 336), 33 wt % octanol and 20 wt % kerosene was contacted in a pressure vessel with an aqueous solution comprising 50 wt % sodium lactate. The aqueous and organic phases were mixed at ambient temperature under $CO_2$ pressure of 30 atmospheres for 6 hours. The organic phase was then separated under pressure from the aqueous solution and from the sodium bicarbonate formed in the reaction. It contained 10 wt % lactic acid. Butanol was added to it (38.3 g butanol per 78.5 g organic phase). The mixture was heated to 166° C. in a closed pressure vessel and kept at this tempeature for 6 hours. After cooling the organic phase was analyzed by gas chromatography. About 82% of the lactic acid there was converted to butyl lactate. The latter was practically totally recovered from the organicd phase by distillation at 40 mmHg.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of purified lactic acid values from an aqueous feed solution containing lactic acid, lactic acid salt, or mixtures thereof, comprising:
   a) bringing said feed solution into contact with a substantially immiscible anion exchanger to form a substantially water-immiscible phase comprising an anion exchanger-lactic acid adduct;
   b) effecting a condensation reaction in said substantially water-immiscible phase between a carboxylic moiety of said lactic acid adduct and a moiety selected from a hydroxyl moiety and a primary or secondary amine moiety to respectively form a lactic acid ester or amide product; and
   c) separating the formed lactic acid ester or amide product from the anion exchanger.

2. A process for the recovery of purified lactic acid values from an aqueous feed solution containing lactic acid, lactic acid salt, or mixtures thereof, comprising:
   a) bringing said feed solution into contact with a substantially immiscible anion exchanger to form a substantially water-immiscible phase comprising an anion exchanger-lactic acid adduct;
   b) effecting a condensation reaction in said substantially water-immiscible phase between a carboxylic moiety of said lactic acid adduct and a hydroxyl moiety to form a lactic acid ester; and
   c) separating the formed lactic acid ester from the anion exchanger.

3. A process according to claim 1, wherein said anion exchanger is a basic extractant comprising a water immiscible amine as the main active component, and there is formed a substantially water-immiscible extract phase comprising an anion exchanger-lactic acid adduct.

4. A process according to claim 1, wherein said anion exchanger is a solid anion exchanger.

5. A process according to claim 1, wherein said contact with a substantially immiscible anion exchanger is carried out in the presence of an added alkanol.

6. A process according to claim 1, wherein the separated lactic acid ester has a purity of at least 99%.

7. A process according to claim 1, wherein said lactic acid ester is a product of the reaction of at least two lactic acid molecules.

8. A process according to claim 1, wherein said lactic acid ester is selected from the group consisting of lactoyl lactate and lactide.

9. A process according to claim 1, wherein said lactic acid ester is lactide.

10. A process according to claim 9, wherein said lactide contains less than 20 milliequivalents of free acid.

11. A process according to claim 1, wherein said separated lactic acid ester is hydrolyzed to form the lactic acid.

12. A process according to claim 3, wherein said basic extractant comprises an alkanol.

13. A process according to claim 3, wherein alkanol is added to said extract prior to effecting the condensation reaction.

14. A process according to claim 1, wherein said lactic acid ester is a product of the reaction of at least one lactic acid molecule and at least one alkanol molecule.

15. A process according to claim 1, wherein said separated lactic acid ester is hydrolyzed to form the lactic acid and the alkanol.

16. A process according to claim 15, wherein said alkanol formed upon hydrolyzing said lactic acid ester is reintroduced into said basic extractant prior to extraction of more lactic acid, or into said extract prior to effecting the condensation reaction.

17. A process according to claim 3, wherein co-extracted water is removed from said extract prior to said condensation reaction.

18. A process according to claim 1, wherein water formed in said condensation reaction is removed either sequentially or substantially simultaneously with said condensation reaction.

19. A process according to claim 1, wherein said lactic acid product is separated from said anion exchanger either sequentially or substantially simultaneously with said condensation reaction.

20. A process according to claim 1, wherein said separation is into an aqueous solution.

21. A process according to claim 1, wherein said separation is into a solvent, which solvent is immiscible or of low miscibility with the anion exchanger.

22. A process according to claim 1, wherein said separation is into the vapor phase.

23. A process according to claim 20, wherein separation into said aqueous solution induces hydrolysis.

24. A process according to claim 1, wherein said condensation reaction is conducted at a temperature higher than 100° C.

25. A process according to claim 1, wherein said condensation reaction is conducted at sub-atmospheric pressure.

26. A process according to claim 1, wherein said condensation reaction is conducted in the presence of a carrier gas.

27. A process according to claim 1, wherein said anion exchanger is at least a moderately strong base, with an apparent basicity corresponding to a pKa of at least 3.5.

28. A process according to claim 1, wherein said anion exchanger is at least a moderately strong base, with an apparent basicity corresponding to a pKa of at least 4.

29. A process according to claim 1, wherein the lactic acid-to-amine molar ratio in said extract is less than one.

30. A process according to claim 1, wherein the purity of all the recovered lactic acid values in said product is higher than 99%.

31. A process according to claim 1, wherein said lactic acid ester forms a separate phase from said extract.

32. A process according to claim 1, wherein said aqueous feed solution results from fermentation.

33. A process according to claim 1, wherein said lactic acid salt is selected from a group consisting of sodium, calcium, ammonium lactate and mixtures thereof.

34. A process according to claim 1, wherein said contact with a substantially immiscible anion exchanger forms, in addition to the amine lactic acid adduct, a basic product.

35. A process according to claim 34, wherein said basic product is selected from the group consisting of ammonia, carbonates and bicarbonates of ammonia, of alkali and of alkaline earth metals.

36. A process according to claim 1, wherein said contact with a substantially immiscible anion exchanger is conducted in a $CO_2$ atmosphere.

37. A process according to claim 1, wherein said aqueous feed solution is at pH of at least 4.5.

38. A process according to claim 1, wherein said condensation is conducted in the presence of a catalyst.

39. A process for the recovery of purified lactic acid values from an aqueous feed solution containing lactic acid, lactic acid salt, or mixtures thereof, comprising:
   a) bringing said feed solution into contact with a substantially immiscible anion exchanger to form a substantially water-immiscible phase comprising an anion exchanger-lactic acid adduct;
   b) effecting a condensation reaction in said substantially water-immiscible phase between a carboxylic moiety of said lactic acid adduct and a reagent comprising a primary or secondary amine moiety to form an amide of lactic acid; and
   c) separating the formed amide of lactic acid from the anion exchanger.

* * * * *